(12) United States Patent
Barone et al.

(10) Patent No.: US 9,102,898 B2
(45) Date of Patent: Aug. 11, 2015

(54) PERFUME

(75) Inventors: Salvatore J. Barone, Staten Island, NY (US); Irina Staina, Branchburg, NJ (US); Loic Bleuez, Ornex (FR)

(73) Assignee: Coty Inc., New York, NY (US)

( * ) Notice: Subject to any disclaimer, the term of this patent is extended or adjusted under 35 U.S.C. 154(b) by 0 days.

(21) Appl. No.: 13/529,480

(22) Filed: Jun. 21, 2012

(65) Prior Publication Data

US 2013/0023592 A1    Jan. 24, 2013

Related U.S. Application Data

(60) Provisional application No. 61/509,364, filed on Jul. 19, 2011, provisional application No. 61/511,288, filed on Jul. 25, 2011.

(51) Int. Cl.
*A61Q 13/00* (2006.01)
*C11B 9/00* (2006.01)
*A61K 8/34* (2006.01)
*A61K 8/81* (2006.01)
*A61K 8/04* (2006.01)

(52) U.S. Cl.
CPC ............ *C11B 9/0015* (2013.01); *A61K 8/046* (2013.01); *A61K 8/34* (2013.01); *A61K 8/8147* (2013.01); *A61K 8/8158* (2013.01); *A61K 8/8164* (2013.01); *A61K 8/8182* (2013.01); *A61K 8/8188* (2013.01); *A61K 8/8194* (2013.01); *A61Q 13/00* (2013.01); *A61K 2800/262* (2013.01); *A61K 2800/52* (2013.01)

(58) Field of Classification Search
CPC .................................. A61K 8/34; A61Q 13/00
USPC ............................................................. 512/2
See application file for complete search history.

(56) References Cited

U.S. PATENT DOCUMENTS

| | | | |
|---|---|---|---|
| 6,270,782 B1 * | 8/2001 | Sawyer et al. | ................ 424/401 |
| 2001/0046507 A1 | 11/2001 | Dietz et al. | |
| 2002/0155076 A1 | 10/2002 | Lanzendorfer et al. | |
| 2004/0047826 A1 | 3/2004 | Brown | |
| 2005/0227907 A1 * | 10/2005 | Lee et al. | .......................... 512/4 |
| 2014/0128311 A1 | 5/2014 | Barone et al. | |

FOREIGN PATENT DOCUMENTS

| | | |
|---|---|---|
| EP | 1715841 B1 | 5/2007 |
| WO | WO-92/00722 A1 | 1/1992 |
| WO | WO-98/51262 A2 | 11/1998 |
| WO | WO 9851262 A2 * | 11/1998 ............... A61K 7/00 |

(Continued)

OTHER PUBLICATIONS

Defintion of "Particle". Obtained Sep. 25, 2014 at http://dictionary.reference.com/browse/particle.*

(Continued)

*Primary Examiner* — Ling Choi
*Assistant Examiner* — Lanee Reuther
(74) *Attorney, Agent, or Firm* — Schwegman Lundberg & Woessner, P.A.

(57) ABSTRACT

Inventive subject matter disclosed herein includes a perfume that includes water; alcohol; oil in a concentration of about 2 to 20% by weight; a scent imparting constituent; and a stabilizing agent in a concentration effective for imparting a capacity to make a misting spray pattern when the perfume is sprayed through a sprayer.

25 Claims, 5 Drawing Sheets

(56) References Cited

FOREIGN PATENT DOCUMENTS

| WO | WO-02/05771 | A1 | | 1/2002 | |
|---|---|---|---|---|---|
| WO | WO 0205771 | A1 | * | 1/2002 | |
| WO | WO-2004/098556 | A1 | | 11/2004 | |
| WO | WO 2004098556 | A1 | * | 11/2004 | ............... A61K 7/46 |
| WO | WO-2009/053148 | A1 | | 4/2009 | |
| WO | WO 2009053148 | A1 | * | 4/2009 | |
| WO | WO-2013/012515 | A1 | | 1/2013 | |
| WO | WO-2013/012939 | A1 | | 1/2013 | |

OTHER PUBLICATIONS

"International Application Serial No. PCT/US2012/043525, International Search Report mailed Sep. 19, 2012", 4 pgs.

"International Application Serial No. PCT/US2012/043525, Written Opinion mailed Sep. 19, 2012", 6 pgs.

"International Application Serial No. PCT/US2012/047230, International Search Report mailed Oct. 1, 2012", 6 pgs.

"International Application Serial No. PCT/US2012/047230, Written Opinion mailed Oct. 1, 2012", 8 pgs.

"Spanish Application Serial No. 201231128, Office Action mailed Oct. 17, 2012", (w/ English Summary), 4 pgs.

"Spanish Application Serial No. 201231128, Response filed Nov. 13, 2012 to Office Action mailed Oct. 17, 2012", (w/ English Claims), 9 pgs.

"International Application Serial No. PCT/US2012/043525, International Preliminary Report on Patentability mailed Sep. 6, 2013", 7 pgs.

"International Application Serial No. PCT/US2012/047230, International Preliminary Report on Patentability mailed Jan. 30, 2014", 10 pgs.

"Polyacrylate Crosspolymer-6 (Sepimax Zen)", [Online] Retrieved From Internet: <http://www.nicnas.gov.au/PUBLICATIONS/CAR/NEW/PLC/PLC0900SR/plc977.asp>, (2009).

"U.S. Appl. No. 13/822,583, Restriction Requirement mailed Jan. 9, 2015", 5 pgs.

"Brazilian Application Serial No. BR1120140012199, Amendment filed May 28, 2014", 5 pgs.

"Brazilian Application Serial No. BR1120140012229, Amendment filed May 30, 2014", 6 pgs.

"Nuevos productos Clariant [Clariiant launches new youth concept at in-cosmetics 2011", (w/ English Translation). [online] Retrieved From Internet: <http://www.pressreleasefinder.com/item.asp?id=13555>, (2011), 4 pgs.

"Spanish Application Serial No. 201231128, Office Action mailed Apr. 2, 2014", (w/ English Summary), 7 pgs.

"Spanish Application Serial No. 201231128, Office Action mailed Sep. 25, 2014", 3 pgs.

"Spanish Application Serial No. 201231128, Office Action mailed Oct. 18, 2013", 5 pgs.

* cited by examiner

PERFUME

RELATED APPLICATION

This application claims the benefit of priority, under 35 U.S.C. §119(e), to U.S. provisional application Ser. No. 61/509,364, filed Jul. 19, 2011 and 61/511,288, filed Jul. 25, 2011, which are incorporated herein by reference in their entireties.

FIELD

Inventive subject matter disclosed herein relates to perfume embodiments that include one or more of a perfume oil or essential oil, one or more alcohols, a stabilizing agent and, for some embodiments, a stable suspension of particles.

BACKGROUND

Human beings have been applying fragrances to themselves for thousands of years. The ancient Egyptians, believed to be among the first users, applied perfumed oil and incense to themselves. Some of the earliest recorded chemists made perfume and used the process of distillation to extract scents from natural materials such as flowers. Other methods of scent extraction have included maceration and solvent extraction. Over the course of human history, scents have mirrored the cultures that created them. One gruesome example was a fragrance called, "Parfum a la Guillotine," created during the French Revolution. The trend of fragrance reflecting the larger culture continues to the present day.

IN THE DRAWINGS

SUMMARY

Figure 1:
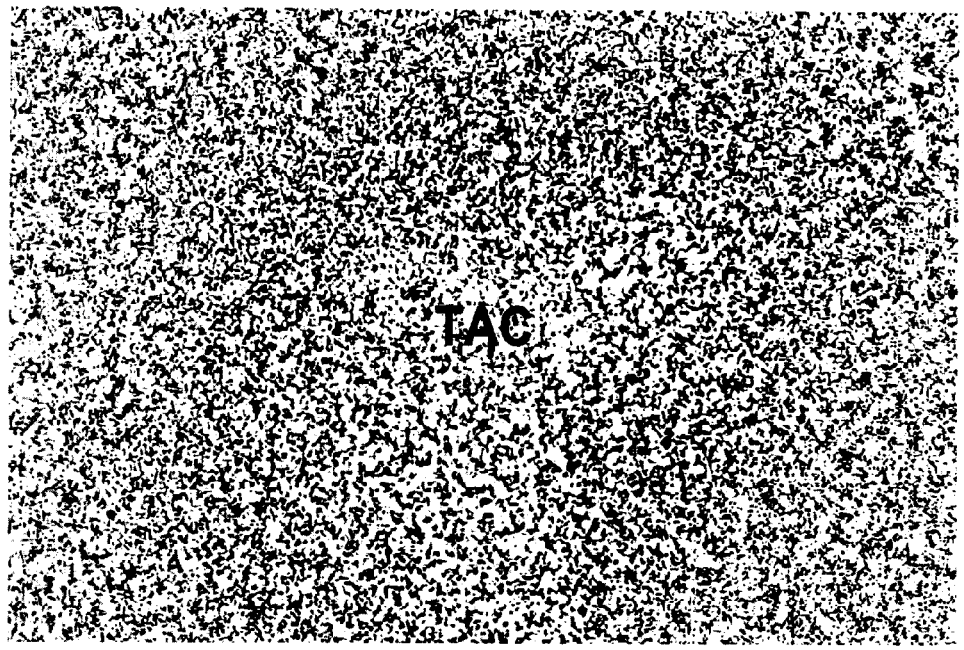
FIG. 1 illustrates a top plan view of one spray pattern made with a perfume embodiment that includes Aristoflex TAC.

Inventive subject matter disclosed herein includes a perfume that includes water; alcohol; oil capable of being stabilized at a concentration of 20% by weight when in the perfume; a scent imparting constituent; and a stabilizing agent in a concentration effective for imparting a capacity to make a misting spray pattern when the perfume is sprayed through a sprayer having a higher than normal pre-compression spring.

Inventive subject matter also includes a perfume comprising: water; alcohol; carboxyvinyl polymer, a neutralizing agent and 2 Na EDTA in concentrations effective for stabilizing the rheology, viscosity and suspending ability of the fragrance, and effective for imparting a capacity to make a misting spray pattern when the perfume is sprayed through a sprayer having a higher than normal pre-compression spring.

The perfume also includes oil in a concentration of at least 8% by weight; and scent blended with the oil.

Inventive subject matter additionally includes a perfume comprising: water; alcohol; oil in a concentration of 2 to 20% by weight; a suspension of particles; and ammonium Acryloyl Dimethyltaurate/Carboxyethyl Acrylate crosspolymer in a concentration effective for stabilizing the rheology, viscosity and suspending ability of the fragrance and effective for imparting a capacity to make a misting spray pattern when the perfume is sprayed through a sprayer having a higher than normal pre-compression spring, wherein the perfume has a transparent appearance;

Another inventive embodiment includes a perfume comprising: Ethanol 190 proof; Fragrance Oil in a concentration of 8 to 10% by weight; Polyacrylate crosspolymer-6 in a concentration effective for stabilizing the rheology, viscosity and suspending ability of the fragrance and effective for imparting a capacity to make a misting spray pattern when the perfume is sprayed through a sprayer having a higher than normal pre-compression spring, wherein the perfume has a transparent appearance; Water; Black Iron Oxide, and a UV filter Another embodiment includes a perfume comprising: alcohol in a concentration of at least about 75 percent by weight; a thickener that includes a polyacrylate crosspolymer-6, and water, in concentrations effective for imparting a capacity to make a misting spray pattern when the perfume is sprayed through a sprayer.

Another perfume embodiment includes water; alcohol in a concentration of 76 wet weight percent; oil in a concentration capable of being within the range of about 2 to 20% by weight; a scent imparting constituent; and a stabilizing agent comprising

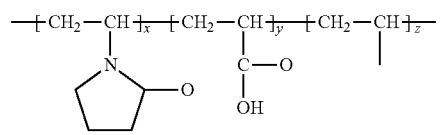

in a concentration effective for imparting a capacity to make a misting spray pattern when the perfume is sprayed through a sprayer.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Disclosed herein are inventive embodiments for a hydro-alcoholic perfume having a viscosity within a range of 30 to 1000 centipoise, the hydro-alcohol-based, perfume embodiments including water, one or more alcohols, a fragrance oil in a concentration that is capable of being up to 20% by weight, and one or more scents. Inventive embodiments also include stabilizing agent for stabilizing all of the constituents of the fragrance formulation and for promoting a fine mist spray pattern embodiment when the perfume is sprayed through a spray pump. While a viscosity range of 30 to 1000 centipoise is described, it is understood that the viscosity may be higher for some embodiments. Each of the stabilizing polymers disclosed herein imparts to the formulation of alcohol, water, fragrance oil and scent imparting material, a particular rheology behavior. As a consequence, for embodiments that include a stabilizer, the specific range and spray mist pattern embodiments disclosed herein depend upon the stabilizing polymer(s) employed, which are disclosed herein.

Figure 6:
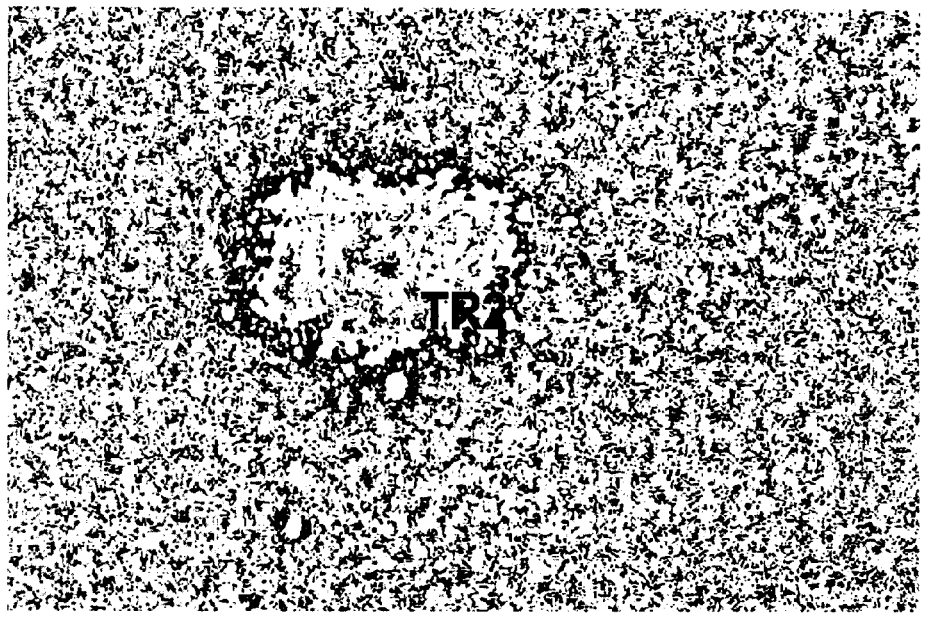
FIG. 6 illustrates a top plan view of one spray pattern made with a perfume embodiment that includes Pemulen TR-2.
Figure 7:
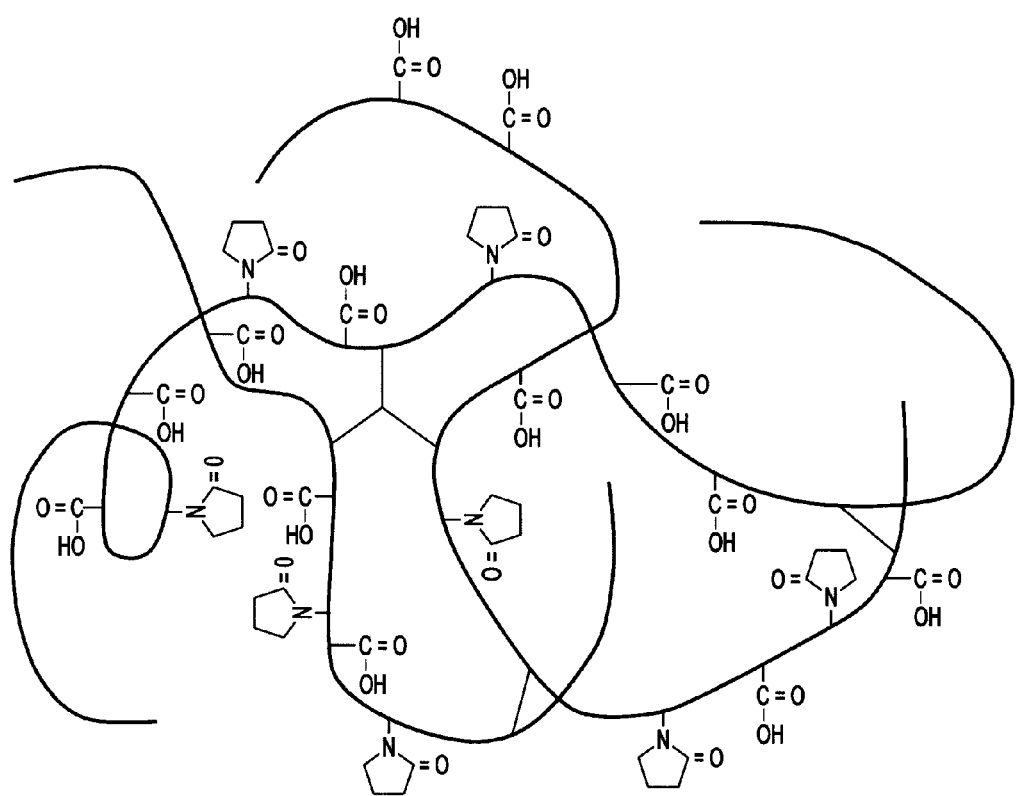
FIG. 7 illustrates a chemical structure view of Ultrathix P-100.

This fine mist spray pattern is unexpected in that it occurs across the spectrum of hydro-alcoholic perfume formulation embodiments. The spray pattern is also unexpected in view of the elevated viscosity of the perfume and high fragrance oil loading. For instance, a hydro-alcoholic perfume formulation, such as is disclosed herein, thickened with a material such as Pemulen TR-2, a formulation of acrylates/C (10-30) alkyl acrylate crosspolymer, manufactured by Lubrizol, does not have an adapted rheology necessary to obtain a misting spray patter embodiment described herein, as shown in FIG. 6.

Additionally, the stabilizing agent, in combination with other constituents, imparts phase stability, rheology stability and particle suspension stability, for perfume formulation embodiments that include particles. Some perfume formulation embodiments disclosed herein also include a stable suspension of particles wherein the fragrance oil and stable suspension impart one or more sensory experiences to a consumer.

Some perfume embodiments impart sensory experiences directed to one or more of sight or appearance of the perfume such as crystal clear transparency, especially when the perfume is in a clear, transparent container, such as a bottle. Other perfume embodiments display a sparkle from light reflecting, glittering particles when in the transparent container. For other perfume embodiments, fragrances or scents impart sensations experienced by the consumer upon inhaling the scent of the fragrance, and feel of the perfume upon application of the perfume formulation to skin. Other perfume embodiments impart multiple sensory experiences or impart a combination of sensory experience and non-sensory benefits.

The perfume formulation embodiments disclosed herein include one or more alcohols, one or more fragrance oils in concentrations up to 20% by weight, one or more scent imparting constituents, water and one or more stabilizing agents. The one or more stabilizing agents impart to the perfume, a desirable misting spray pattern embodiments when sprayed from a pump sprayer having a higher than normal pre-compression spring. For some perfume formulation embodiments that include particles, the stabilizing agent stabilizes the suspension of particles in the alcohol, fragrance oil, water formulation. For some embodiments, the particles have a concentration of less than one percent by weight.

The perfume formulation embodiments described herein are surprising and unexpected because they maintain long term stability with a very high concentration of fragrance oils and they display a desirable misting spray pattern when sprayed through a sprayer having a higher than normal pre-compression spring. These features also exist in perfume embodiments that include particles.

Water in the hydro-alcoholic formulation embodiments disclosed herein is present in a concentration of up to about 25% percent by weight, and the one or more alcohols are present in a concentration range of about 45% to 80% by weight. For some embodiments, the alcohol is a 190 proof SDA 40 B ethanol. Any low molecular weight alcohol, such as isopropanol, can be used with or without a denaturant and with any denaturant commercially available. Some perfume embodiments also include a C(12) to C(22) alcohol in order to decrease evaporation of the alcohol from the perfume formulation. The water is, for some embodiments, demineralized water. Some perfume embodiments include a fragrance fixing complex, such as disclosed in EP1715841B1, which is herein incorporated by reference. The fragrance fixing complex includes 0.01 to 10% by weight of a hydrophobic, alcohol-soluble, carboxylated acrylates/octylacrylamide copolymer and 0.01 to 10% by weight of a hydrolyzed jojoba ester, wherein percents are related to the total weight of the cosmetic composition.

Some formulation embodiments also include high fragrance oil concentrations in concentrations up to about 20% by weight. As discussed, a stable perfume formulation that includes this elevated loading of fragrance oil is unexpected. The stability of formulations that include both particles and the elevated loading of fragrance oil is even more unexpected.

The perfume formulation embodiments disclosed herein form a very stable gel, for some embodiments, and a stable, thickened formulation for other embodiments. This stability is demonstrated by stability of rheology, viscosity and, for some embodiments, particle suspending ability for all viscosities of perfume formulation embodiments.

In one embodiment, the particle suspension stabilizing agent employed, ammonium acryloyl dimethyltaurate/carboxyethyl-acrylate-crosspolymer, has the commercial name, Aristoflex TAC (code TRM04192), and is manufactured by Clariant of New Jersey. The Aristoflex TAC copolymer has the following chemical formula:

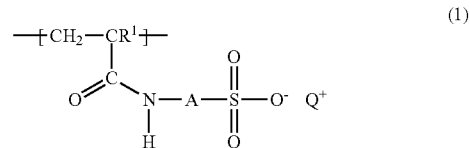

The Aristoflex TAC includes polymers having one or more of the structural repeat units of the formula (1)

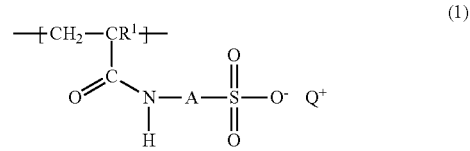

in which $R^1$ is hydrogen, methyl or ethyl and A is $C_1$-$C_3$-alkylene, and $Q^+$ is $H^+$, $NH_4^+$, $Li^+$, $Na^+$, $K^+$, ½ $Ca^{++}$, ½ $Mg^{++}$, ½ $Zn^{++}$ or ⅓ $Al^{+++}$, and the degree of neutralization of the structural units of the formula (1) is from 50 to 100 mol %, preferably from 80 to 100 mol %, more preferably from 90 to 100 mol %, and with more particular preference from 95 to 100 mol %, and b) one or more of the structural repeat units of the formula (2)

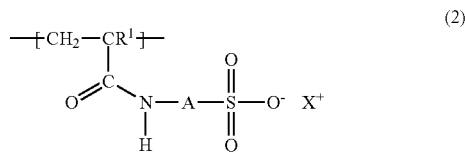
(2)

in which $R^1$ and A have the definition of $R^1$ and A from formula (1) and $X^+$ is $[HNR^5R^6R^7]^+$, where $R^5$, $R^6$, and $R^7$ independently of one another can be hydrogen, a linear or branched alkyl group having 1 to 22 carbon atoms, a linear or branched, singly or multiply unsaturated alkenyl group having 2 to 22 carbon atoms, a $C^6$-$C^{22}$-alkylamidopropyl group, a linear mono-hydroxyalkyl group having 2 to 10 carbon atoms or a linear or branched di-hydroxyalkyl group having 3 to 10 carbon atoms, and where at least one of the radicals $R^5$, $R^6$, and $R^7$ is not hydrogen, with the proviso that the molar ratio of the structural units of the formula (1) in which $Q^+$ is $NH^{4+}$, $Li^+$, $Na^+$, $K^+$, $Ca^{++}$, $Mg^{++}$, $Zn^{++}$ or $Al^{+++}$ to the structural units of the formula (2) is from 97:3 to 55:45, and the corresponding alkylammonium chlorides XCI possess a critical micelle concentration (CMC)<15 g/l, and d) 0% to 8%, preferably 0.01% to 5%, by weight of crosslinking structural units originating from monomers having at least two olefinic double bonds.

The Aristoflex TAC copolymer has an average molecular weight range from 1000 to 3,000,000 MWU. The Aristoflex TAC copolymer is usable to aid in the suspension of particles. The Aristoflex copolymer is usable in clear gels, low viscosity, and low pH formulations.

The Aristoflex TAC copolymer is a pre-neutralized, cross-linked sulfonic acid polymer that is a 100% active powder, which swells easily on addition to surfactant systems. The Aristoflex TAC copolymer eliminates viscosity loss of surfactant solutions at low temperature. The Aristoflex TAC copolymer creates a yield force and stabilizes color particles even at low concentrations, low viscosities, and an acidic pH.

The Aristoflex TAC is used to stabilize perfume formulation embodiments that include water, alcohol in concentrations up to about 79% by weight, fragrance, and, for some embodiments, a suspension of particles.

Figure 8:
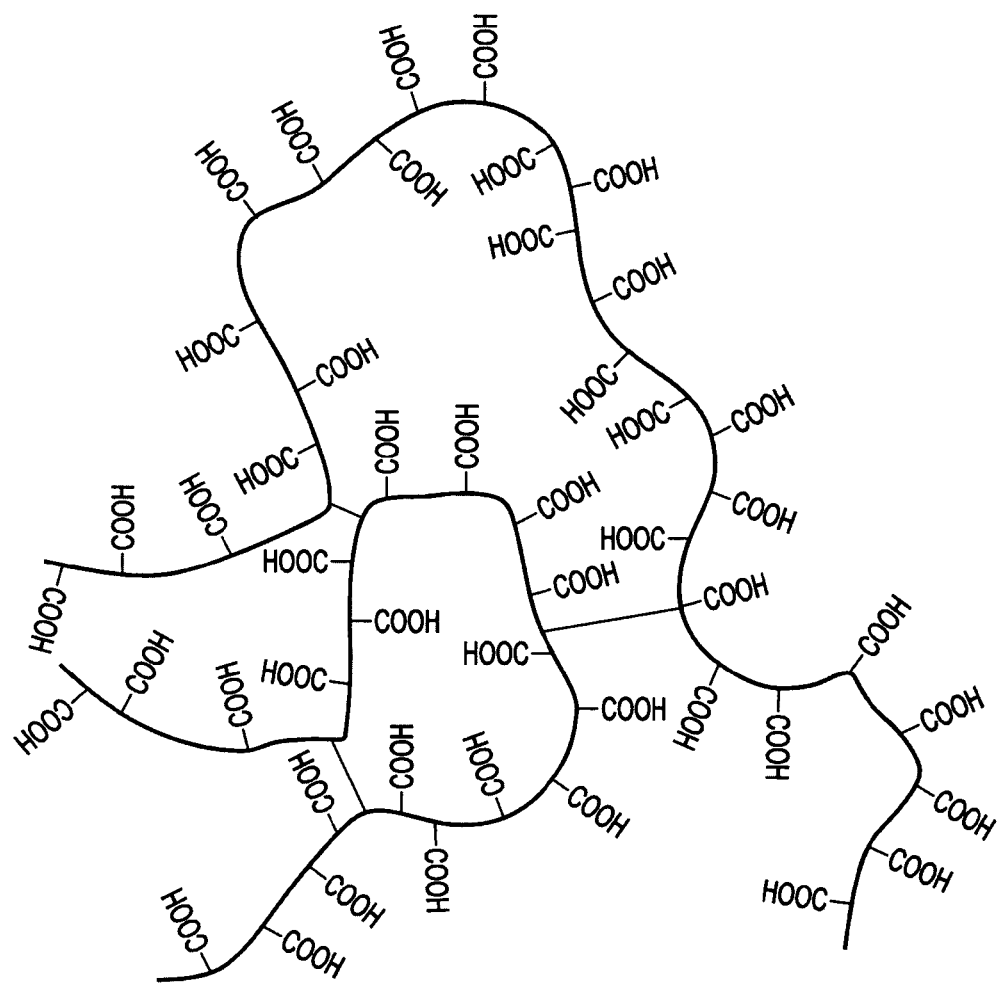
FIG. 8 illustrates a chemical structure view of Carbopol 980.

In another embodiment, a thickener such as Carbopol 980 is employed as the stabilizing agent. Carbopol 980 is a cross-linked polyacrylate polymer, manufactured by Lubrizol. The chemical structure of Carbopol 980 is shown in FIG. 8. Other formulations having a high cross-linked acrylic acid polymer having the same rheological properties as Carbopol 980, include Carbopol 940 and Carbopol Ultrez, manufactured by Lubrizol and Tego Carbomer 140 and Tego Carbomer 340D, manufactured by Evonik. The Carbopol 980 is used to stabilize perfume formulation embodiments that include an alcohol such as ethanol in concentrations as high as 68% by weight, fragrance oil as high as 10% by weight, and water in a concentration up to about 25% by weight. The Carbopol 980 stabilized perfume formulations imparts a stable pre-selected rheological profile and, in combination with other constituents, enables the fragrance formulation to make a fine mist when sprayed from a pump sprayer having a higher than normal pre-compression spring.

Another thickener usable in perfume embodiments disclosed herein includes a polyacrylate crosspolymer-6, having commercial name Sepimax Zen, manufactured by Seppic, of Puteaux, France.

One other thickener usable in perfume embodiments disclosed herein includes Ultrathix P-100, manufactured by ISP. Ultrathix P-100 has the following chemical structure:

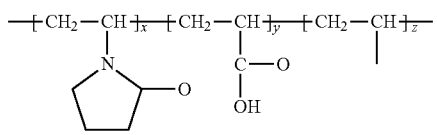

See also FIG. 8

The Aristoflex TAC, Carbopol 980, Sepimax Zen, Ultrathix P-100 and other polymers disclosed herein are also usable, in combination with other constituents, to further maintain the suspension of particles in the perfume formulation so that the suspension does not separate and settle, for perfume formulation embodiments that include a particle suspension. These other constituents include one or more surfactants, especially for fragrance formulation embodiments having higher water concentration.

Surfactants are usable to reduce the ethanol concentration of a perfume embodiment. Surfactants include disodium laureth sulfosuccinate, alone or in mixture with disodium lauryl sulfosuccinate.

In another embodiment of the invention, one or more non-ionic emulsifiers can be added to the perfume composition. Suitable non-ionic emulsifiers which can be used include polyethylene glycol hydrogenated castor oil with 2 to 200 polyethylene glycol units, preferably PEG-40 hydrogenated castor oil and/or PEG-60, hydrogenated castor oil, polysorbate 20, polysorbate 40, polysorbate 60, oleth-5, oleth-10, oleth-20 or PPG-1-PPG-9, lauryl glycol ether and mixtures thereof. Solubilisant LRI (Sensient) and other commercial blends specifically developed for fragrance solubilization can be used as well. In some cases, anionic and/or cationic surfactants maybe used alone or in combination to solubilize the fragrance oil in the hydro alcoholic media.

Each of these stabilizers also impart to the perfume embodiments disclosed herein, a capacity to make a desirable spray pattern when sprayed with a spray pump having a higher than normal pre-compression spring that produces the shear required to propel the perfume through the spray nozzle. One type of spray pump having a higher than normal pre-compression spring is obtained from Rexam SP22+/Dose 80, obtained from Rexam PLC of Milbank, London SW1P, UK. Desirable spray patterns are shown in FIGS. 1, 2, 3 and 4. These spray patterns were prepared with perfume formulations having a concentration of fragrance oil of 10% by weight. The spray patterns were made by spraying the sprayer a distance of twelve cm+/−1 cm from a surface receiving the spray. Spraying was performed three times by the same person in order to increase the contrast between the spray and the paper in order to obtain better quality images.

The surface receiving the spray was paper obtained from Staples. The paper was vertically positioned on a fixed metal frame. A light was positioned on the rear of the paper and was not directed on the paper in order to increase contrast. A camera was used to capture images of the spray patterns. The camera was positioned 54 cm+/−1 cm from the paper. The camera was not used with a flash and was a reflex self focus.

Figure 2:
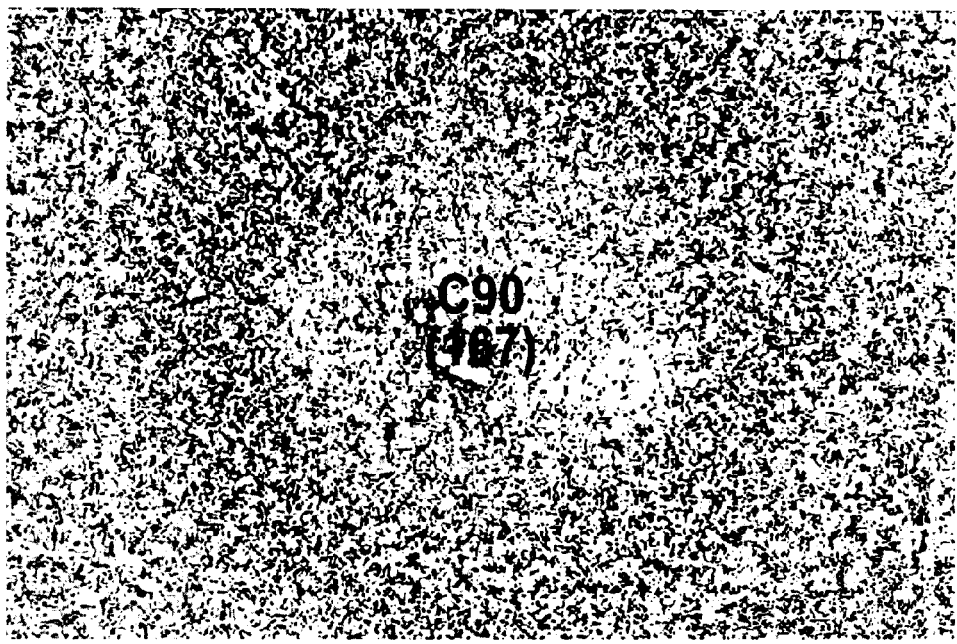
FIG. 2 illustrates a top plant view of one spray pattern made with a perfume embodiment that includes Carbopol 980.
Figure 3:
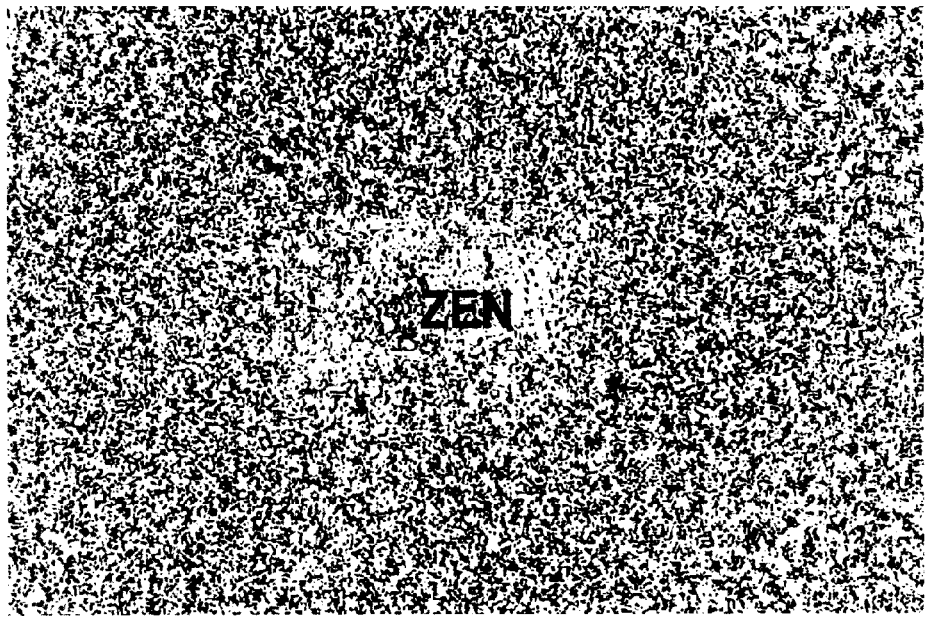
FIG. 3 illustrates a top plan view of one spray pattern made with a perfume embodiment that includes Sepimax Zen.
Figure 4:
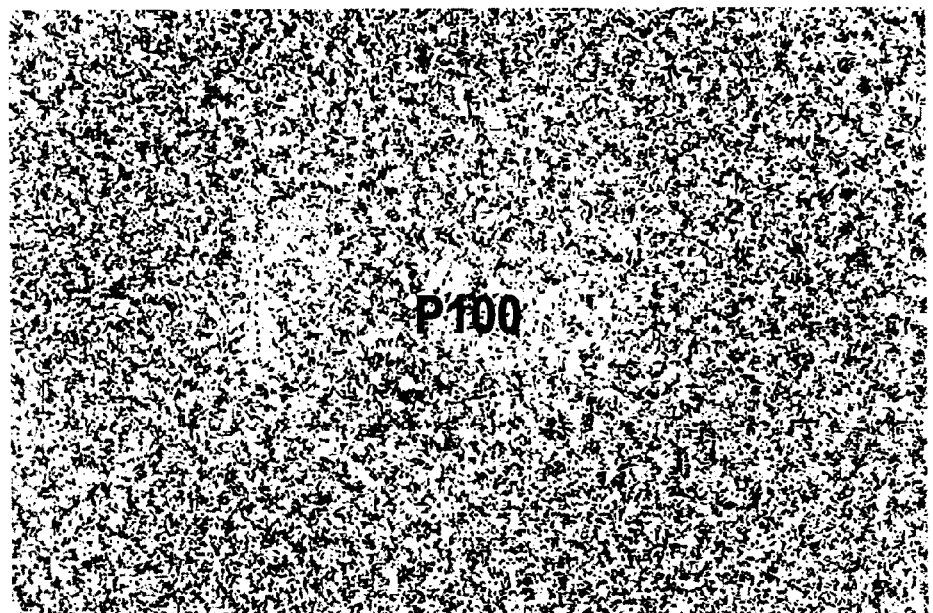
FIG. 4 illustrates a top plan view of one spray pattern made with a perfume embodiment that includes Ultrathix P-100, obtained from ISP.
Figure 5:
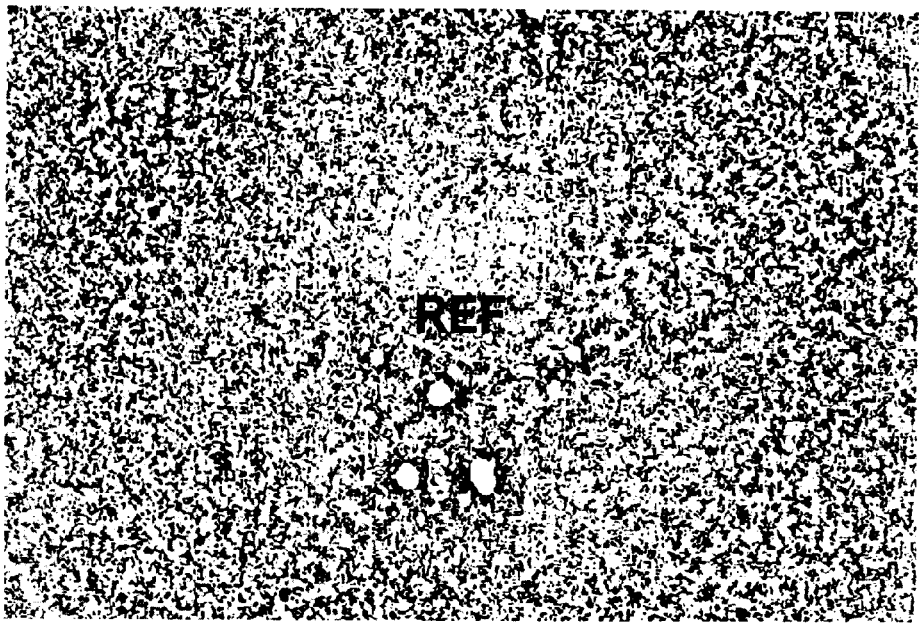
FIG. 5 illustrates a top plan view of a spray pattern made with a perfume that was free of a stabilizer.

FIG. 1 shows a spray patterns made with a perfume embodiment that includes 10% fragrance oil by weight and Aristoflex TAC. The spray pattern is characterized by a mist of fine droplets. FIG. 2 illustrates a perfume embodiment that includes 10% fragrance oil by weight and Carbopol 980. This spray pattern is also characterized by a mist of fine droplets. FIG. 3 illustrates a perfume embodiment that includes 10% fragrance oil by weight and Sepimax Zen, which is also characterized by fine droplets. FIG. 4 illustrates a perfume embodiment that includes 10% fragrance oil and Ultrathix P-100, obtained from ISP and is also characterized by fine droplets. Control and contrast spray patterns are shown in FIGS. 5 and 6. FIG. 5 illustrates a spray pattern made with a perfume formulation that includes 10% fragrance oil but does not include a stabilizing agent. The spray pattern is characterized by a fine mist of droplets. FIG. 6 illustrates a spray pattern made with a perfume formulation that includes 10% fragrance oil and a Pemulen TR 2 thickener obtained from Lubrizol which is a typical polymer showing long flow rheology as measured with a Brookfield RVT DVII@25 C using Mobil 2 speed 50, is 208 cps. The spray pattern is characterized by large drops.

Other constituents that may be added include antioxidants, ultraviolet inhibitors, solvents, surfactants and quenchers. Antioxidants and quenchers include vitamins such as vitamin C and derivatives thereof, for example, ascorbic acetate, ascorbic phosphate, and ascorbic palmitate; vitamin A and derivatives thereof; folic acid and derivatives thereof; vitamin E and derivatives thereof such as Tocopheryl Acetate, Tocopheryl Linoleate, Tocopheryl Phosphate; flavones or flavonoids; amino acids, such as histidine, glycine, tyrosine, tryptophan, and derivatives thereof; carotenoids and carotenes such as α-carotene, β-carotene and mixtures thereof, with the same proviso as above. Well-known antioxidants are for example BHT, BHA, Tinogard® TT, Tinogard® TS, Tinogard® NOA (from Ciba), TBHQ, Propyl Gallate, Vitamin E TPGS (Tocophersolan), Parsol Guard® (from DSM) and various mixtures known under Covi-OX® (from Cognis) or Oxynex® (from MERCK); Quenchers as Tinoguard® Q (from Ciba), Spectrasolv® (from The Hallstar Company) or Oxynex® ST (from Merck). Ultraviolet inhibitors include benzo phenone 3.

Solvents include DPG, PG, isopropyl myristate, ethylhexyl palmitate, diethyl phthalate, triethyl citrate, Isododecane, Isohexadecane, Isoeicosane, isoparaffin fluids, $C_{13}$-$C_{30}$ alkanes, Hydrogenated Dodecene, Hydrogenated Dododecene, Hydrogenated Polydecene, Hydrogenated Polydodecene, Hydrogenated Tridodecene, Hydrogenated Polyisobutene, mineral oils, and a mixture of two or more thereof, or the solvent is a linear silicone of the Dimethicone type, a cyclic silicone or a mixture thereof.

Some perfume embodiments include opacifiers that include the following: Acusol OP303P Opacifier; Acusol 302P Opacifier; Acusol OP304 emulsion; Opulyn 303B Opacifier; Opulyn 303B Opacifier; Opulyn 303K Opacifier; Opulyn 301 Opacifier (or Syntran 5903-5904-5905-5907); Opulyn 305 Opacifier; Opulyn PQG Opacifier; Lytron 284; Lytron 288; Lytron 300; Lytron 651; Lytron 170 Lytron 30 Lytron 300; Neocryl B-1000; Opacifier 43.009; Allianz OPT or Soltex OPT polymers.

Three specific examples of perfume embodiments include the following:

Examples are presented herein for exemplary purposes and are not intended to limit embodiments of inventive subject matter.

Example 1

| Ingredient | Wet % |
| --- | --- |
| Demineralized Water | 10.67 |
| GA Black Oxide | 0.08 |
| Aristoflex TAC | 0.25 |
| Ethanol 190P | 79 |
| Fragrance | 10 |
|  | 100 |

The range of formulation embodiments that include the Aristoflex TAC include alcoholic formulations and aqueous formulations. The alcoholic formulation embodiments have the following features:
Alcohol: about 82% to 85% by weight
Water: 5% minimum
Black oxide: 0.05%
Aristoflex TAC: from 0.15% to 2.0 to 3.0% by weight
Fragrance: up to 10% by weight
For aqueous formulation embodiments:
Water: about 70% to 80% by weight
Solvent: about 9% to 17% by weight
Black oxide: 0.05% by weight
Aristoflex TAC: from 0.9% to 2.0 to 3.0%
Fragrance: up to 10% by weight Example 2

| Ethanol 190 Proof | 68% by weight |
| --- | --- |
| Fragrance Oil | 10% |
| Carbopol 980 | 0.55% |
| Neutrol TE | 1.1% |
| 2Na EDTA | 0.1125% |
| Water | 20.24% |

Color (black Iron Oxide) and solubilizer and UV filter made to 100%.

The sodium EDTA was used to stabilize the viscosity of the Carbopol 980 over an extended period of storage. While Carbopol 980 is disclosed, it is believed that other acrylic homopolymers may be usable in the formulation of Example 2. Carbopol 980 and any other suitable polymer impart a suitable rheology profile and enables the fragrance formulation to make a fine mist when sprayed. For some embodiments, the fragrance oil concentration ranges from 2 to 16%.

The Neutrol TE is a base and functions to chemically neutralize the carboxylic acid moieties of Carpopol 980 to form mucilages. While Neutrol TE is described, other suitable neutralizing agents include aminopropanol such as AMP, manufactured by Angus; diisopropanolamine and Triisopropanolamine, manufactured by Dow, and PEG-15 cocamine, such as Ethomeen C-25, manufactured by Akzo. As used herein, the term "mucilage" refers to a fully swollen polymer, an equilibrium of neutralized Carbopol polymer in its polyanionic state.

For one embodiment, the perfume embodiment of Example 2 had a viscosity of 606 cps, measured with a Brookfield RVT DVII viscometer at 25 degrees Centigrade, Mobil 2 Speed 50. This embodiment included calcium sodium borosilicate particles and titanium dioxide particles, manufactured by BASF.

For another embodiment, the perfume embodiment of Example 2 had a viscosity of 976 cps, measured with a Brookfield RVT DVII viscometer at 25 degrees Centigrade, Mobil 2 Speed 50. This embodiment included cellulose powder raw material, manufactured by Daito Kasei.

Example 2A

| Raw Material Name | Wet % |
|---|---|
| Phase A | |
| Ethanol 190P | 53.5% |
| Reflecs Dimensions Glittering White G 1305 | 00.02% |
| FD&C Red No. 4 PG&Q | 00.10% |
| Phase B | |
| Symphony 221480H Fragrance compound | 10.00% |
| Cremophor RH-40 | 3.00% |
| Tenox BHT | 00.05% |
| EUSOLEX 9020 | 00.10% |
| Phase C | |
| DI Water | 16.8% |
| Ethanol 190P | 10.5% |
| Carbopol 980 | 00.7% |
| Phase D | |
| DI Water | 14.12% |
| Trilon BD | 00.2% |
| Neutrol TE | 1.5% |

Cremophor RH-40 is a nonionic solubilizer and emulsifying agent. The main constituent of Cremophor RH 40 is PEG-40 hydrogenated castor oil, which, together with hydrogenated castor oil, forms the hydrophobic part of the product. The hydrophilic part includes of polyethylene glycols OE.

The Tenex BHT is an antioxidant, 2,6 ditertiarybutyl-4-methyl phenol.

EUSOLEX 9020, manufactured by Merck, is an ultraviolet inhibitor, Avobenzone.

Different ratios of Carbomir 980/Disodium EDTA are usable to control viscosity.

Trilon BD is the disodium salt of ethylenediamine tetraacetic acid, dehydrate, and is manufactured by BASF. Other chelating agents such as 3 and 4 Na EDTA may be used to stabilizer the Carbomer.

Example 2B

| Raw Material | Wet % |
|---|---|
| Phase A | |
| Ethanol 190P | 53.5% |
| Cellulo Beads D-10 | 2.0% |
| Phase B | |
| ALENCON 475268 FD Fragrance Compound | 10.0% |
| Cremophor RH-40 | 2.0% |

-continued

| Raw Material | Wet % |
|---|---|
| Tenex BHT | 0.05% |
| EUSOLEX 9020 | 0.10% |
| Phase C | |
| DI Water | 16.8% |
| 190 Proof Ethanol | 10.5% |
| Carbopol 980 | 0.7% |
| Phase D | |
| DI Water | 2.65% |
| Trilon BD | 0.2% |
| Neutrol TE | 1.5% |

Example 3

One other perfume embodiment includes a higher viscosity gel-based perfume made with a stabilizer that includes the Seppimax Zen polyacrylate crosspolymer-6. The perfume formulation includes the following:

| Constituent | Percent by Weight |
|---|---|
| Ethanol 190 proof | 75% |
| Fragrance Oil | 10% |
| Sepimax Zen | 0.55% |
| Water | 14.27% |
| Black Iron Oxide + UV filter | Added to 100% |

The viscosity of this formulation, measured with a Brookfield RVT DVII viscometer, at 25 degrees Centigrade, Mobil 2 Speed was 660 cps.

While Example 3 discloses black iron oxide particles as a coloring agent, other particulate constituents may be used. Additional perfume formulations were included wherein instead of black iron oxide, particles of calcium aluminum borosilicate and titanium dioxide and silica and iron oxide were included. For these embodiments, viscosity, as measured with a Brookfield RVT DVII viscometer at 25 degrees Centigrade and Mobil 2 Speed 50 was 260 cps.

Example 4

Formulation embodiments disclosed herein also include those imparting an excellent mist pattern using conventional, commercially available pumps. One formulation embodiment is the following:

| Ingredient | Wet % | Wet Wt. |
|---|---|---|
| Phase 1 | | |
| Alcohol SDA 40B 190P | 76.0 | 228.0 g |
| Water, Deionized | 5.6 | 16.8 g |
| Sepimax, ZEN | 0.3 | 0.9 g |
| Water, Deionized | 4.1 | 12.3 g |
| Phase 2 | | |
| Platinum 296335B | 6.0 | 18.0 g. |
| Phase 3 | | |
| Water, Deionized | 7.9 | 23.9 g. |
| Titanium Dioxide | 0.002 | 0.006 |

The formula embodiment of Example 4 forms a fine mist when sprayed with conventional pumps for EDT (Eau De Toilette) bulk as, for instance, Aptar 30MS-15 70 mcl; and Aptar PMP-VP4-100-CS-15-FEA+PRS-108A-104-HDS, manufactured by AptarGroup having worldwide locations.

As used herein, the term, "suspending agent" refers to an agent capable of stabilizing suspended particles in an alcoholic or aqueous/alcoholic medium. The suspending agents disclosed herein include CARBOPOL 980 and Aristoflex TAC.

As used herein, the term, "gel," refers to a colloid in which a solid disperse phase forms a network in combination with a fluid continuous phase, resulting in a viscous sol.

The word, "particle" as used herein refers to a discrete portion of material that has mass and dimension. Particles are elements of a suspension. Particles include microparticles and nanoparticles. Microparticles have a diameter ranging from about 1 to 1000 microns. Nanoparticles have a diameter ranging from 1 to 1000 nanometers. Particles also include macroparticles (i.e. 1001 um to 0.5-1 cm) microparticles and nanoparticles. For some embodiments, the fragrance formulation has a low weight load of particles.

The term, "perfume," as used herein refers to perfumes, colognes eau de toilettes, after-shave lotions, pre shave, face waters, tonics, and other fragrance containing compositions for application directly to skin. Perfume formulation embodiments disclosed herein include one or more alcohols. Some perfume formulation embodiments disclosed herein are stored in a transparent vessel such as a perfume bottle and are dispensed through a spray nozzle. A conventional spray pump and nozzle dispenser is usable.

The terms, "fragrance," "scent," and "perfume oils" as used herein refer to substances for modifying the smell/odor of a product providing a smell/odor to a person. Mixtures of natural essential oils or synthetic fragrances are possible. 'Essential oils, which are smelling substances derived by physical processes, distillations, from plants or spices are also subsumed under the term "perfume oils."

Perfume Formulation Embodiments Wherein the Sensory Experience is a Visual Effect How a perfume formulation appears to a consumer when the perfume is in a bottle or other container is one sensory experience. With the appearance-based embodiments described herein, the combination of the stabilized perfume oil-hydro-alcoholic formulation displays a stability of appearance and rheology over a long period of storage. For some perfume formulation embodiments that include a suspension, particles within the stable suspension impart one or more of an appearance-based sensory experience that includes color, opacity, light emission, light reflection and combinations of these types of visual sensory effects. In one embodiment, the visual appearance of the perfume is transparent, including colored and transparent. Visual effects are formed, for some embodiments, by the suspension of particles. Current hydrophobic and/or hydrophilic dyes alone or in combination are usable to color the perfume embodiments disclosed herein.

Specific particle types within the suspension include sparkling, reflective particles, dyed particles, encapsulated particles and microspheres enclosing color or opacity or light emitting or reflecting particles. These particle embodiments include one or more of titanium oxide, mica, other iron oxides such as yellow, red and brown, in addition to black and tin oxide.

Other usable colored particles include particles having ferric ammonium ferrocyanide (blue), manganese violet, ultramarine blue, chrome oxide (green), talc, lecithin modified talc, zeolite, kaolin, lecithin modified kaolin, titanium dioxide (white) and mixtures thereof. Other useful particle pigments include pearlescents such as mica, bismuth oxychloride and treated micas, such as titanated micas and lecithin modified micas that include. mica, coated with varying thickness of titanium dioxide and particles that include thin film optics imparting brilliant luster and a broad range of interference colors and multicolor effect. For some embodiments, particles that include tiny light emitting diodes, LED's, or luminescent materials impart to a perfume formulation a capacity for emitting light, either continuously or intermittently.

Other types of particles imparting a visual effect include particles that include an interference pigment having a multilayer structure. The core of the interference particle includes a flat substrate with a refractive index below 1.8.

For some embodiments, the particles are coated with a coating such as a polysaccharide. For one embodiment, the particles are hydrophilic GA black oxide particles that have been surface treated with galactoarabinan. The particles were obtained from Color Techniques of South Plainfield, N.J., as product number GA-7403. Galactoarabinan is a polysaccharide obtained as an extraction from the larch tree, *Larix*. The GA black oxide particle sizes are in a range of 20 to 200 microns. The galactoarabinan coated particles are resistant to oxidation and dispersed within a fluid with a particle suspending agent, such as Aristoflex or CARBOPOL 980.

For some perfume formulation embodiments displaying a visual effect, the perfume formulation displays layers of colors or color gradation or an opacity gradation. In particular, for some embodiments, two or more stable particle suspensions are formed as part of a perfume formulation, enclosed in a vessel, each suspension formed based upon particle size, particle density, surface charge, or combination of these particle attributes. The two or more suspensions stabilize in separate and distinct areas of the fragrance formulation, within the storage bottle. For these embodiments, the consumer views a perfume having separate layers of color or gradations of the same or different coloring or opacity or other types of visual appearances within the vessel. The layers or gradations or other appearances are viewable because each of the particle suspensions displays different colors or different opacities or different refractive indices or different reflective features.

For other embodiments, the alcohol-based fragrance portion of the perfume formulation has one color or opacity and the particle suspension or suspensions have another color or opacity.

When the perfume formulation is sprayed onto skin, the particle suspension disintegrates and the particles separate from the rest of the perfume formulation. Colored and opaque particles disperse on a user's skin and appear colorless. However, glitter does appear on the user's skin. Perfume embodiments disclosed herein surprisingly display to consumers dramatic colors and appearances when in a vessel but do not impart these colors and appearances onto the skin, hair and clothes of consumers when the perfume is applied, unless the particles include a material such as glitter.

For one embodiment, the perfume formulation has a black color and appearance when viewable in a perfume bottle. However, the perfume is colorless when applied to a consumer's skin. For this embodiment, the suspension of particles, such as black oxide particles, impart a black color to the perfume formulation when the formulation is stored in the bottle. Once the suspension is disrupted by spraying through the dispenser, the perfume formulation appears colorless on a consumer's skin. For embodiments where the perfume includes a suspension of particles that impart color and glitter, the sprayed perfume does not impart color when sprayed, but does impart glitter.

Perfume Formulation Embodiments Wherein the Sensory Experience is Olefactory

An olfactory experience occurs when the perfume formulation is dispensed from a vessel such as a bottle. Typically, perfume formulation embodiments disclosed herein are dispensed with a spray nozzle and generate a fine mist. Conventional perfume spray nozzles are usable for dispensing perfume formulation embodiments disclosed herein. Olfactory experiences occur at the time the perfume formulation is sprayed onto skin of an end user and after it has resided on the skin for a period of time.

Perfume formulation embodiments of the present invention include one or more of stabilized fragrance oils or perfume oils. Examples of perfume oils are extracts of flowers such as lily, rose, jasmine, neroli or ylang-ylang, stems and leaves such as geranium, patchouli or petitgrain, fruits such as anis, coriander, cumin or juniper, fruit skins such as bergamot, citrus or orange, roots such as macis, angelica, cardamom, iris or calmus, wood such as pine, sandalwood, guaiac, cedar or rose, herbs and grasses such as tarragon, lemon grass, salvia or thyme, needles and branches such as pine or fir, resins and/or balms such as galbanum, elemi, benzol, myrrh, olibanum or opoponax. Further, animal raw materials such as zibet and/or castoreum can be used as perfume oils. Typical synthetic fragrances are for instance products from the ester type, ether type, aldehyde type, detone type, alcohol type and/or hydrocarbon type.

Useful perfume oils include Galaxolide (hexamethylhexahydrocyclopentabenzo-pyran, 50% of Isopropyl Myristate), Ethylene Brassylate (1,4-dioxacyclohepta-decan-5,17-dione), Habanolide (CAS-No.: 423773-57-3), Globanone (cyclohexa-dec-8-en-1-one), Musk Ketone (1-(4-tert-butyl-2,6-dimethyl-3,5-dinitrophenyl)-ethanone), Musk Xylol (1-tert-butyl-3,5-dimethyl-2,4,6-trinitrobenzene), Trimofix O (2,5,10-trimethyl-2,5,9-cyclododecatrien-1-yl methyl ketone & isomers), Sandalore (5-(2,2,3-trimethyl-3-cyclopentenyl)-3-methylpentan-2-ol), Boisambrene (ethoxymethyl-cyclododecyl ether,), Nerolidol (3,7,11-trimethyl-1,6,10-dodecatrien-3-ol), Cedramber (cedryl methyl ether), Iso E Super (1-(1,2,3,4,5,6,7,8-octahydro-2,3,8,8-tetramethyl-2-naphtalenyl)-ethan-1-one), Irisantheme ((E)-3-methyl-4-(2,6,6-trimethyl-1-cyclohex-2-enyl)but-3-en-2-one), Damascone Alpha ((E)-1-(2,6,6-trimethyl-1-cyclohex-2-enyl)but-2-en-1-one), Orange Bresil (essential oil, for instance available from Eau-Douce, France), Orange EO from Brazil (CAS: 8028-48-6), Lilial (INCI name: butylphenyl methylpropional), Aldehyde Alpha Hexyl Cinnamic (hexyl cinnamal), Farnesol (3,7,11-trimethyl-2,6,10-dodecatrien-1-ol), Bacdanol (2-ethyl-4-(2,2,3-trimethyl-3-cyclopenten-1-yl)-2-buten-1-ol), Ebanol (3-methyl-5-(2,2,3-trimethyl-3-cyclopenten-1-yl)-4-penten-2-ol), Guaiac Wood Acetate (CAS 61789-17-1), Cedrenyl Acetate (CAS-No.: 1405-92-1), Hexyl Salicylate, Verdox (2-tert-butylcyclohexyl acetate), Cis-3 Hexenyl Salicylate, Linalool, (3,7-dimethyl-1,6-octadien-3-ol,) Linalyl Acetate (CAS-No.: 115-95-7) or Benzyl Salicylate, Hedione (methyl dihydrojasmonate), Dihydromyrcenol (2,6-dimethyl-7-octen-2-ol) and mixtures thereof. Other perfume oils are also possible according to Int. Cosmetic Ingredient Dictionary and Handbook, 12$^{th}$ ed. 2008, Vol. 3, p. 3193-3200 (edited by CTFA, Washington D.C., USA).

The stabilized oils include one or more of esters such as benzyl acetate, ester, ethers, aldehydes, ketones, alcohols, and hydrocarbon types. Esters include benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate, and benzyl salicylate. Ethers include, for example, benzyl ethyl ether; Aldehydes include, for example, the linear alkanals having 8 to 18 carbon atoms, citral, citronellal, citronellyloxyacetaldehyde, cyclamenaldehyde, hydroxycitronellal, lilial and bourgeonal; Ketones include, for example, the ionones, alpha-isomethylionone, and methyl cedryl ketone; Alcohols include anethol, citronellol, eugenol, geranionol, linalool, phenylethyl alcohol, and terpineol; and the hydrocarbons include terpenes and balsams. Preference is given to using mixtures of different odorants which in unison produce a pleasant fragrance note.

The definition of aromatic (odorant) substances also comprises such substances as e.g. ethyl vanilline, vanilline (4-hydroxy-3-methoxy-benzaldehyd), heliotropine (1,3-benzodioxole-5-carboxaldehyde), helional (alphamethyl-1,3-benzodioxole-5-propanal), coumarin (1,2-Benzopyrone), ethyl maltol (2-ethyl pyromeconic acid), ethyl acetate, ethyl acetoacetate, 2-methyl pyrazine, linalool oxide (6-methyl-2-(oxiran-2-yl)hept-5-en-2-ol), hydroxycitronelial (7-hydroxy-3,7-dimethyloctanal), ethylphenol, benzyl acetate, allyl amyl glycolate or mixtures thereof.

One olfactory experience is caused by fragrance that is stabilized within the alcohol-based fragrance formulation. The scent dispensed by this fragrance is dispersed in a fine mist. Additionally, for some perfume formulation embodiments that include particles, the stable, suspended particles include encapsulates or microspheres or both that retain, additional scent that is the same as the alcohol-based scent of the perfume formulation. Encapsulation includes in situ encapsulation and entrapment systems, such as those including Cellulobeads or encapsulates that contain perfume when added to the perfume formulation. Encapsulation and entrapment systems include those that allow fragrance oil fixation, absorption/adsorption, on a solid particle. These fragrance oil absorption/adsorption systems include particles such as porous PMMS, silica, zeolite, allyle methacrylate cross-polymer and so forth.

For some embodiments, one or more additional scents that complement the alcohol-based, non-particulate scent are employed. For some embodiments, the particles include coatings or capsules that dissolve on the skin at different times, resulting in a time release for scent and an extended effectiveness of the perfume formulation. This feature extends the fragrance sensation much longer than occurs when the liquid alone is sprayed. For other embodiments, the particles of the suspension include scents that complement the fragrance in the alcohol water solution. These particles release their scent(s) either in concert with the spraying of the perfume formulation onto skin or in a time release fashion. For some embodiments, the particles release two or more scents in an orchestrated fashion over time to provide a user with a dynamic unexpected olfactory sensation.

Thus, the use of a suspension of scent-containing particles suspended in an aqueous solution that also includes scent creates novel perfume formulations having complex and interesting orchestrated olfactory releases. For instance, consumers can perceive top notes immediately upon application, multiple and graded middle notes that become sensed over time and multiple and graded base notes that follow the middle notes.

The perfume embodiments described herein enable the creation of new and heretofore not possible fragrance combinations of, for example, floral, oriental, wood, leather, Chypre, Fougere, green bright floral, aquatic, citrus, fruity gourmand, and others wherein the perfume formulation is presented to the user in an aesthetic and pleasing container and appearance.

The combination of the alcohol-based fragrance and scent-containing particles also is usable to combine aroma therapy scents in an orchestrated system, such as has been disclosed. The aroma therapy system disclosed herein is usable to create a long lasting and every changing experience that enables a consumer to relax or avoid food cravings as two examples only.

Perfume Formulation Embodiments Wherein the Sensory Experience is Tactile

One tactile experience occurs when a user touches the perfume formulation when it is in a vessel. The perfume formulation embodiments disclosed herein feel softer than perfume formulation embodiments that do not include a stabilizing agent, without being sticky to the touch.

The tactile sensation also occurs when the perfume formulation is dispensed from the vessel onto the skin of a consumer. For some embodiments, the perfume formulation includes conditioning particles within the stable suspension, that impart a softness or suppleness to skin to which the fragrance is applied. These conditioning particles include one or more of constituents for moisturizing, for wrinkle prevention and for stimulating new cell growth. Moisturizers include aloe vera, althea, avocado oil, balm mint, burdock, shea butter, camphor, chamomile, isodecyl oleate and other conditioning agents.

Perfume Formulation Embodiments Wherein the Perfume Formulation Imparts Other Attributes One type of embodiment, wherein the perfume formulation has other attributes is one in which one type of encapsulate imparts a particular appearance to a perfume and when applied to skin, and adds emollients or moisturizers or other beneficial material to skin, when the encapsulate is broken. For these embodiments, the particles within the suspension include one or more of chelating agents, skin conditioners, emollients, preservatives, buffering agents, antioxidants, chelating agents, opacifiers, acetic acid for bleaching; acetyl hexapeptide for controlling wrinkles, horse chestnut seed extract for promoting circulation; amino guanidine for preventing collagen damage; arctium majus extract for treating acne, psoriasis, eczema, ascorbic acid, beta-carotene, bisabolol, bromelain, Ceramides, *Cucumis Sativa* for tightening skin, jojoba oil, tocopherol, Vitamin A, and similar classes of optional ingredients known to persons skilled in the art Particulates disclosed herein constitute a dispersion that, for some embodiments, forms a network in combination with the suspending agent and alcohol-water fragrance solution. For some embodiments, the particle suspension and suspending agent form a sol, having a predetermined viscosity that is suitable for an application. The perfume is applied to a consumer's skin by atomizing the fragrance with a spray nozzle. The particles are stabilized by the suspension stabilizing agent.

For one or more embodiments, the particles are treated with a coating that renders the particles more dispersible in an alcohol water fragrance formulation. For other embodiments, the particles are not coated. For some embodiments, the suspending agent and particles build viscosity of a fragrance product.

For some embodiments, particles include encapsulation systems.

The perfumee formulation embodiments disclosed herein are capable of remaining stable within a container such as a bottle for a long period of time when exposed to a wide range of temperature and over a broad range of pH. For some inventive embodiments, the perfume formulation also includes a transparent vessel for holding the formulation and a dispenser for dispensing the formulation.

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. A perfume comprising:
   Water;
   Alcohol;
   Oil in a concentration within the range of about 2 to 20% by weight;
   a scent imparting constituent;
   one or more surfactants effective for solubilizing the oil in the water and alcohol; particles dispersed uniformly throughout the perfume that impart one or more visual effects to the perfume viewable when the perfume is in a transparent vessel and a stabilizing agent comprising ammonium acryloyl dimethyltaurate/carboxyethyl acrylate crosspolymer; in a concentration effective for stabilizing rheology, viscosity, and particle suspension and imparting a capacity to make a misting spray pattern when the perfume is sprayed through a sprayer, wherein the one or more visual effects is not viewable when sprayed onto a surface.

2. The perfume of claim 1, wherein the ammonium acryloyl dimethyltaurate/carboxyethyl acrylate crosspolymer has a concentration of about 0.08 to 0.25 percent by weight.

3. The perfume of claim 1, wherein the scent imparting constituent is blended with the oil.

4. The perfume of claim 1, wherein the alcohol is ethanol.

5. The perfume of claim 1, wherein the visual effect is a color that is black when viewed in the vessel.

6. The perfume of claim 1, wherein the particles impart a gradation of color.

7. The perfume of claim 1, wherein the particles impart two or more colors to the perfume observable when the fragrance is in a clear bottle.

8. The perfume of claim 1, further comprising particles that impart an olfactory sensory experience to an end user.

9. The perfume of claim 8, wherein the particles release a scent that is the same as the alcohol-based fragrance.

10. The perfume of claim 8, wherein the particles release a scent that is different from the alcohol-based fragrance.

11. The perfume of claim 8, wherein the particles release scent in a time-release fashion.

12. The perfume of claim 8, wherein the fragrance is usable as aroma therapy.

13. The perfume of claim 1, further comprising particles that impart a tactile sensory experience to an end user.

14. The perfume of claim 13, wherein the particles impart a soft sensory experience.

15. The perfume of claim 13, wherein the particles impart a cool or warm sensory experience.

16. The perfume of claim 13, wherein the particles impart a minty sensory experience.

17. The perfume of claim 1, further comprising particles that impart a conditioner to the skin of a user.

18. The perfume of claim 1 wherein the visual effect comprises a sparkle from light reflecting, glittering particles.

19. The perfume of claim 1, wherein the fragrance oil comprises one or more scent imparting constituents.

20. The perfume of claim 19 wherein the reflecting, light reflecting glittering particles are selected from one or more of titanium oxide, mica, other iron oxides such as yellow, red and brown, black and tin oxide.

21. The perfume of claim 1 wherein the visual effect comprises particles that include one or more of ferric ammonium ferrocyanide (blue), manganese violet, ultramarine blue, chrome oxide (green), 30 talc, lecithin modified talc, zeolite, kaolin, lecithin modified kaolin, titanium dioxide (white) and mixtures thereof.

22. The perfume of claim 1, wherein the visual effect comprises one or more pearlescents such as mica, bismuth oxychloride and treated micas, such as titanated micas and lecithin modified micas that include mica, coated with varying thickness of titanium dioxide and particles that include thin film optics imparting brilliant luster and a broad range of interference colors and multicolor effect.

23. The perfume of claim 1, wherein the visual effect comprises one or more particles that include tiny light emitting diodes, LED's, or luminescent materials that impart to a perfume formulation a capacity for emitting light, either continuously or intermittently.

24. The perfume of claim 1, wherein the visual effect comprises particles that include an interference pigment having a multilayer structure.

25. The perfume of claim 1, wherein the particles impart a gradation of opacity observable when the fragrance is in a clear bottle.

* * * * *